(12) United States Patent
Kim

(10) Patent No.: US 10,973,524 B2
(45) Date of Patent: Apr. 13, 2021

(54) DEVICE FOR TRANSCATHETER TREATMENT FOR TRICUSPID REGURGITATION

(71) Applicant: TAU PNU MEDICAL CO., LTD., Busan (KR)

(72) Inventor: June-Hong Kim, Busan (KR)

(73) Assignee: TAU-PNU MEDICAL CO., LTD., Busan (KR)

( * ) Notice: Subject to any disclaimer, the term of this patent is extended or adjusted under 35 U.S.C. 154(b) by 500 days.

(21) Appl. No.: 15/318,070

(22) PCT Filed: Jun. 16, 2015

(86) PCT No.: PCT/KR2015/006040
§ 371 (c)(1),
(2) Date: Dec. 12, 2016

(87) PCT Pub. No.: WO2015/194816
PCT Pub. Date: Dec. 23, 2015

(65) Prior Publication Data
US 2017/0119489 A1 May 4, 2017

(30) Foreign Application Priority Data
Jun. 17, 2014 (KR) .................. 10-2014-0073518

(51) Int. Cl.
*A61B 17/12* (2006.01)
*A61M 25/01* (2006.01)
(Continued)

(52) U.S. Cl.
CPC .... *A61B 17/1204* (2013.01); *A61B 17/00234* (2013.01); *A61B 17/0493* (2013.01);
(Continued)

(58) Field of Classification Search
CPC ...... A61F 2/2451; A61F 2/2442; A61F 2/011; A61F 2/013; A61F 2/24; A61F 2/0105;
(Continued)

(56) References Cited

U.S. PATENT DOCUMENTS

2003/0233142 A1 12/2003 Morales et al.
2004/0210240 A1 10/2004 Saint
(Continued)

FOREIGN PATENT DOCUMENTS

| JP | 2002505140 A | 2/2002 |
|---|---|---|
| JP | 2002537909 A | 11/2002 |
| KR | 20110023094 A | 3/2011 |
| KR | 1020110023094 | 3/2011 |
| WO | 0051675 A1 | 9/2000 |
| WO | 2008060553 A1 | 5/2008 |

OTHER PUBLICATIONS

International Search Report of PCT/KR2015/006040.

*Primary Examiner* — Sarah W Aleman

(57) ABSTRACT

The present invention relates to a device for transcatheter treatment for tricuspid regurgitation and, more particularly, to a device for patients suffering from tricuspid regurgitation. The device for transcatheter treatment for tricuspid regurgitation according to a preferred embodiment of the present invention includes: a hollow coronary sinus tube (22) for engaging into coronary sinus tissue; and a hollow tricuspid valve tube (24) for crossing over tricuspid valve tissue and anchoring at interventricular septum tissue, wherein the coronary sinus tube and the tricuspid valve tube are laterally coupled with each other from upper portions thereof by a predetermined length, and lower portions thereof are separated from each other; and the lower portion of the tricuspid valve tube (24) is provided with a blocking part (30) for blocking a space resulting from incomplete closure of the tricuspid valve.

4 Claims, 3 Drawing Sheets

(51) Int. Cl.
*A61B 17/04* (2006.01)
*A61B 90/00* (2016.01)
*A61B 17/00* (2006.01)
*A61F 2/24* (2006.01)
*A61M 25/10* (2013.01)

(52) U.S. Cl.
CPC ........ *A61B 17/12109* (2013.01); *A61B 90/08* (2016.02); *A61M 25/01* (2013.01); *A61B 2017/00243* (2013.01); *A61B 2017/00477* (2013.01); *A61B 2017/00783* (2013.01); *A61B 2090/08021* (2016.02); *A61F 2/2451* (2013.01); *A61M 2025/1052* (2013.01)

(58) Field of Classification Search
CPC ........ A61B 17/12022; A61B 17/12122; A61B 17/1204; A61B 17/0493; A61M 25/09; A61M 2025/0037
See application file for complete search history.

(56) References Cited

U.S. PATENT DOCUMENTS

| | | | |
|---|---|---|---|
| 2008/0183036 A1* | 7/2008 | Saadat | A61B 17/12136 600/104 |
| 2008/0195126 A1 | 8/2008 | Solem | |
| 2010/0191165 A1* | 7/2010 | Appling | A61M 25/0068 604/6.16 |
| 2011/0054597 A1* | 3/2011 | Kim | A61F 2/2451 623/2.37 |
| 2012/0179246 A1* | 7/2012 | Kim | A61F 2/2451 623/2.36 |
| 2012/0316634 A1* | 12/2012 | Shalev | A61B 17/1215 623/1.11 |
| 2013/0211513 A1 | 8/2013 | Rourke et al. | |
| 2013/0325110 A1* | 12/2013 | Khalil | A61F 2/2463 623/2.11 |

* cited by examiner

DEVICE FOR TRANSCATHETER TREATMENT FOR TRICUSPID REGURGITATION

CROSS-REFERENCE TO PRIOR APPLICATIONS

This application is a National Stage Patent Application of PCT International Patent Application No. PCT/KR2015/006040 (filed Jun. 16, 2015) under 35 U.S.C. § 371, which claims the benefit of foreign priority of Korean Patent Application No. 10-2014-0073518 (filed Jun. 17, 2014), the subject matter of which is hereby incorporated by reference in its entirety.

TECHNICAL FIELD

The present invention relates generally to a device for tricuspid regurgitation. More particularly, the present invention relates to a device for transcatheter approach for patients suffering from tricuspid regurgitation, which is an abnormal reverse flow of blood from the right ventricle to the right atrium resulting from incomplete closure of the tricuspid valve between the right ventricle and the right atrium during contraction of the right ventricle of the heart.

BACKGROUND ART

The heart is the center of human circulatory system that pumps blood through our body. It is a muscle that pumps the blood only in one direction. In order for the heart to effectively maintain this unidirectional flow of blood, it must have properly functional valves that prevent backflow through its system, or regurgitation. The heart is divided into four chambers: right and left atrium, and right and left ventricles. The four chambers are connected to the aorta, the inferior and superior vena cava, the pulmonary artery, and pulmonary veins.

The mitral valve (MV) separates the left atrium from the left ventricle while the tricuspid valve (TV) separates the right atrium from the right ventricle. The aortic valve (AV) is located between the left ventricle and the aorta while the pulmonary valve (PV) is located between the right ventricle and the pulmonary artery.

Generally, valves should open and close completely with every heart beat or contraction of the heart. Incomplete opening or closing of the valves causes improper flow of blood. Valvular diseases are divided into two categories, regurgitation and stenosis. Regurgitation is a failure of a valve to close completely and stenosis is a failure of a valve to open completely.

Mitral valve regurgitation (MV) is a common cardiac valve disorder that is caused by incomplete closure of the mitral valve (MV). The MV is located between the left atrium and the left ventricle. Over time, MR places a burden on the heart and worsens its ability to pump blood properly. Such stress on the heart will ultimately lead to heart failure. Traditional treatment for progressive MR requires open heart surgery with sternotomy or thoracotomy. Once the chest is open and access to heart is gained, the MV is either repaired or replaced using an artificial valve. Although very effective, this open-heart procedure is a high risk surgery accompanied by substantial morbidity and prolonged convalescence. Mortality due to surgery itself can be as high as 5%. As a result, the procedure often is not offered to patients who are insufficiently symptomatic to justify the surgical risk and morbidity, or to patients with substantial co-morbidity. It is reserved only for those with severe symptomatic MR.

Meanwhile, the tricuspid valve is a valve constituted by three leaflets (anterior leaflet, septal leaflet, and lateral leaflet) between the right ventricle and the right atrium, and serves to prevent backflow of blood into the right atrium during contraction of the right ventricle by closure of the valve between the right ventricle and the right atrium.

Tricuspid regurgitation refers to a heart disease that is caused by a space between the leaflets resulting from incomplete closure in the process where the three leaflets meet each other to close the valve during contraction of the right ventricle, thereby allowing the blood to flow backwards from the right ventricle to the right atrium. As causes of the tricuspid regurgitation, primary tricuspid regurgitation (TR) accounts for about 25%, which is caused by a defect in the valve itself, and secondary or functional tricuspid regurgitation (TR) accounts for the rest, which is caused by left ventricle dysfunction or mitral valve dysfunction that causes extra strain on the right ventricle, and thereby the tricuspid annulus is enlarged, leading to incomplete closure. Symptoms of tricuspid regurgitation are as follows: fatigue and decreased exercise tolerance due to decreased CO; seroperitoneum due to right-sided heart failure; hepatosplenomegaly due to congestive hepatopathy; and lower limb edema.

As the only standard treatment for tricuspid regurgitation, open heart surgery with sternotomy or thoracotomy, namely an annuloplasty ring technique and a De Vega technique, is widely used. However, these techniques require highly invasive surgery, so they are not usually performed to repair only the tricuspid valve. In other words, these techniques are often offered to a patient with severe symptomatic tricuspid regurgitation, concomitant with mitral valve or coronary artery disease that requires open heart surgery.

Meanwhile, to solve the above mentioned problem of mitral valve regurgitation surgery, research has been conducted to develop a safer and less risky alternative to repair MR, instead of open heart surgery. Much of the research involves use of cardiac catheterization. Recently, the inventor of the present invention presented a thesis regarding "mitral valve cerclage coronary sinus annuloplasty (MVA)" showing outstanding results of MR treatment through applying circular pressure around the mitral annulus. This thesis was filed through PCT as an international patent application (PCT application number PCT/US2007/023836) and has been published (International publication number WO2008/060553).

The aforementioned thesis and published patent application disclosed the mitral cerclage coronary annuloplasty (MVA) procedure. Briefly explained, a catheter is placed in the coronary sinus after accessing the right atrium through the jugular vein, and then a cerclage suture is passed through the proximal septal vein. This cerclage suture can easily pass through the right ventricular outflow tract (RVOT), and this inventor defines this technique as "simple mitral cerclage annuloplasty". Then, the cerclage suture can be easily pulled into the right atrium thus placing the cerclage suture circumferentially around the mitral annulus. Once positioned, tension is applied to the cerclage suture, thereby tightening the mitral valve. This brings together the two leaves of the MV so that they are approximated and reduce the size of its incomplete closure. This procedure can theoretically obtain very similar results to those that conventional surgeries can obtain by directly tightening the mitral annulus, and shows an immediate reduction of MR.

However, since the cerclage wraps around the tricuspid valve (TV), it could affect the function of the TV and damage the valve itself and its appendages. The present invention, as a technique for protecting tissue of the body (heart), discloses a tissue protection device for protecting coronary sinus tissue and tricuspid valve tissue, and has been filed and registered (Korean Patent No. 10-1116867. dated Feb. 8, 2012).

The device is used basically for a patient with mitral valve regurgitation, but since the device is a surgical interventional tool that is inserted into the heart and passes through the tricuspid valve, the device may be used as a surgical tool for tricuspid regurgitation, and thus research thereon is required.

DISCLOSURE

Technical Problem

Accordingly, the present invention has been made keeping in mind the above problems occurring in the related art, and the present invention is intended to propose a device for transcatheter treatment for tricuspid regurgitation, the device capable of being used for transcatheter treatment for tricuspid regurgitation as well as transcatheter treatment for mitral regurgitation, by improving a structure of a device used for mitral valve cerclage coronary sinus annuloplasty.

The present invention is further intended to propose a device for tricuspid regurgitation treatment, the device capable of treating tricuspid regurgitation through a simple catheter technique, which requires minimal invasion without surgery, and capable of expanding therapeutic opportunity through a minimally invasive treatment.

Other and further objects of the invention will appear more fully from the following description.

Technical Solution

In order to achieve the above object, according to one aspect of the present invention, there is provided a device for transcatheter treatment for tricuspid regurgitation, the device including: a hollow coronary sinus tube 22 for engaging into coronary sinus tissue; and a hollow tricuspid valve tube 24 for crossing over tricuspid valve tissue and anchoring at interventricular septum tissue, wherein the coronary sinus tube and the tricuspid valve tube are laterally coupled with each other from upper portions thereof by a predetermined length, and lower portions thereof are separated from each other; and the lower portion of the tricuspid valve tube 24 is provided with a blocking part 30 for blocking a space resulting from incomplete closure of the tricuspid valve.

In a preferred embodiment, the coronary sinus tube 22 and the tricuspid valve tube 24 are made of either a metal coil spring or an elastic synthetic resin.

In a preferred embodiment, the blocking part is in a form of a blocking membrane. More preferably, the blocking membrane includes: an lateral support being connected to the tricuspid valve tube; and a body for blocking blood flow by being connected to a space between support and tricuspid valve tube, wherein the annular support has a stronger structure than the body such that a shape of the blocking membrane is maintained.

In another preferred embodiment, the blocking part is in a form of a balloon.

In another preferred embodiment, device for catheter based treatment for tricuspid regurgitation includes: a hollow cylindrical tube for allowing a cerclage suture to be inserted thereinto, with a hole 21 being provided in a side of the cylindrical tube for allowing a cerclage suture inserted into a coronary sinus to come out from the cylindrical tube, wherein a lower portion of the hollow cylindrical tube below the hole is inserted into a tricuspid valve to crossing over tricuspid valve tissue and anchoring at interventricular septum tissue; and a blocking part 30 provided on a side of the cylindrical tube for blocking a space resulting from incomplete closure of the tricuspid valve.

Advantageous Effects

According to the present invention having the above-described characteristics, a device for transcatheter treatment for tricuspid regurgitation is advantageous in that since the device is configured to be basically used for mitral valve cerclage coronary sinus annuloplasty, and to be additionally provided with a blocking part for blocking a space resulting from incomplete closure of the tricuspid valve, it is possible to be used for transcatheter treatment for tricuspid regurgitation as well as transcatheter treatment for mitral regurgitation.

The device for transcatheter treatment for tricuspid regurgitation is further advantageous in that it is possible to treat tricuspid regurgitation through a simple catheter technique, which requires minimal invasion without surgery accompanied by sternotomy and thoracotomy, and is possible to expand therapeutic opportunity through a minimally invasive treatment.

BEST MODE

Reference will now be made in greater detail to a device for transcatheter treatment for tricuspid regurgitation of the present invention, with reference to the accompanying drawings.

Figure 1:
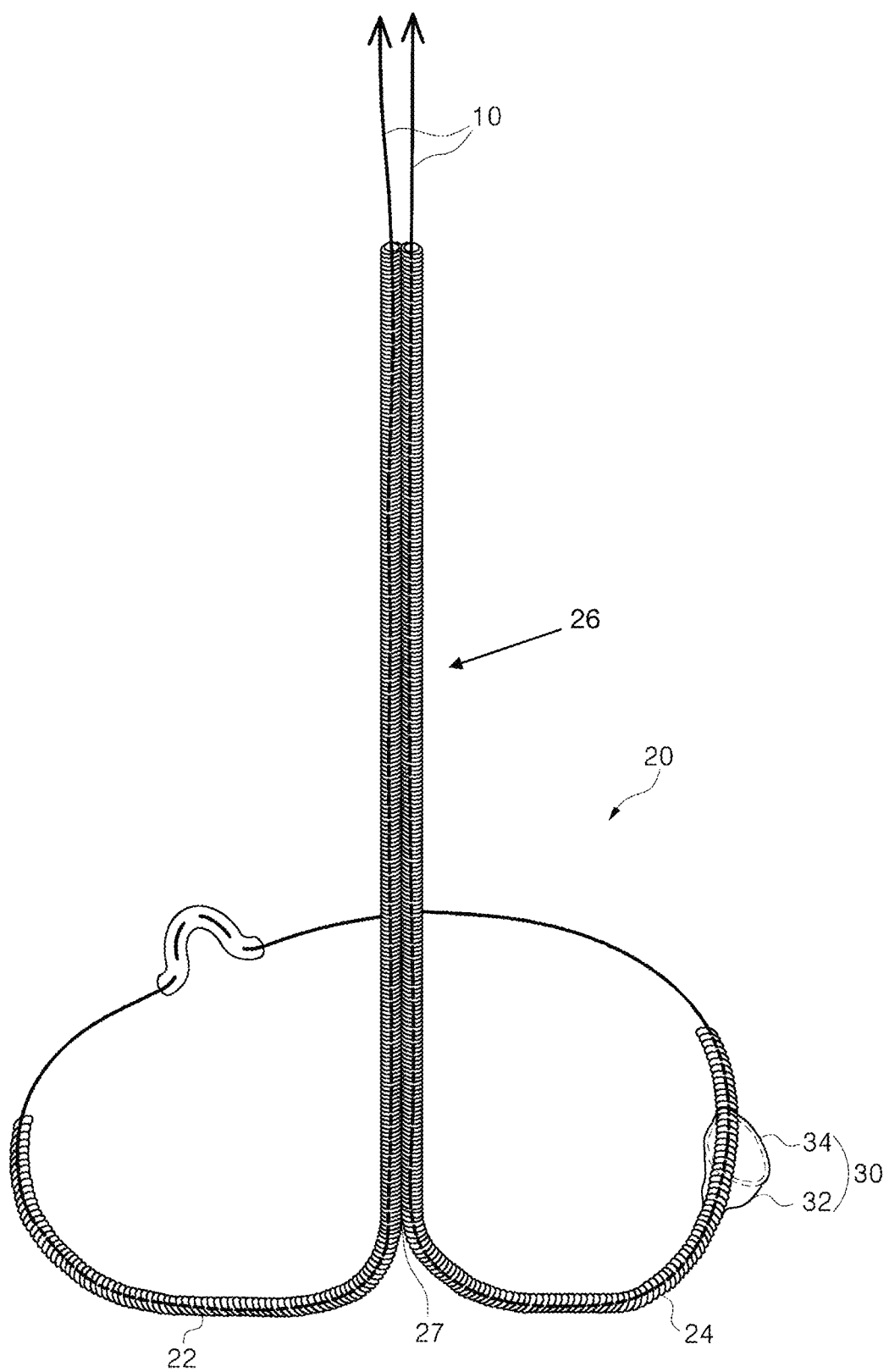
FIG. 1 is a perspective view showing a tissue protection device for transcatheter treatment for tricuspid regurgitation according to a preferred embodiment of the present invention.
Figure 2:
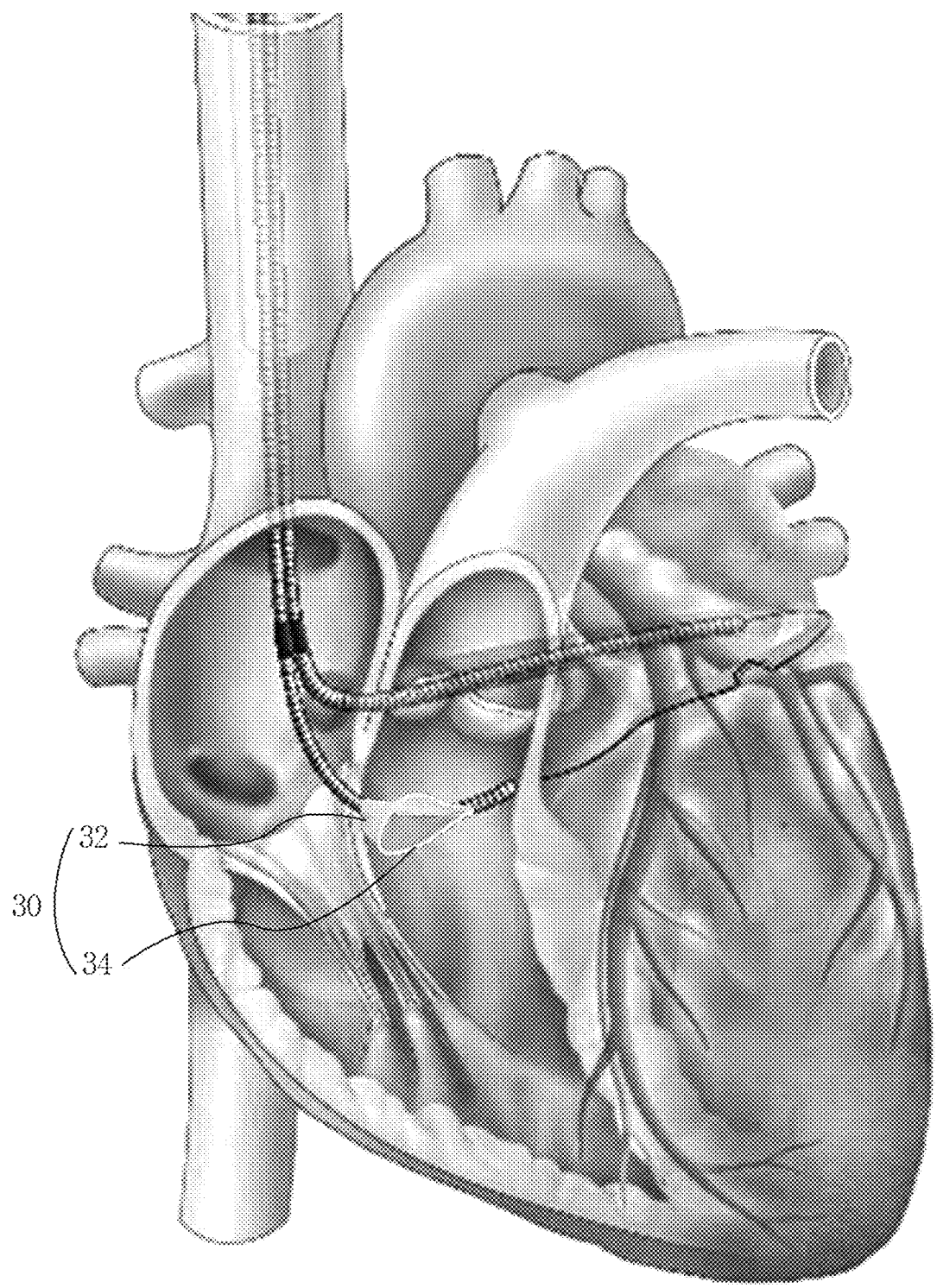
FIG. 2 is an imaginary sectional view of a heart, in which the device for transcatheter treatment for tricuspid regurgitation according to the preferred embodiment of the present invention is placed.

FIG. 1 is a perspective view showing a device for transcatheter treatment for tricuspid regurgitation according to a preferred embodiment of the present invention; and FIG. 2 is an imaginary sectional view of a heart, in which the device for transcatheter treatment for tricuspid regurgitation according to the preferred embodiment of the present invention is placed.

Referring to FIGS. 1 and 2, a device for transcatheter treatment for tricuspid regurgitation of the present invention is configured such that an additional structure is added to a device for mitral valve cerclage coronary sinus annuloplasty and modified to be also used for tricuspid regurgitation.

As described above, secondary or functional tricuspid regurgitation, which is caused by left ventricle dysfunction or mitral valve dysfunction, accounts for most cases of tricuspid regurgitation; and the device for transcatheter treatment for tricuspid regurgitation of the present invention is a modified version of a device for mitral valve cerclage coronary sinus annuloplasty, whereby the device for transcatheter treatment for tricuspid regurgitation of the present invention may be effectively and efficiently used for tricuspid regurgitation as well as mitral valve cerclage coronary sinus annuloplasty.

In FIGS. 1 and 2, a cerclage suture 10 is a thin suture having a thickness of no more than the typical 0.014" that is used in mitral valve cerclage annuloplasty (MVA), in which a length of suture passes through the coronary sinus (CS), the tricuspid valve (TV) and the interventricular septum in a circle form, and comes out of the body. Accordingly, the suture was named a cerclage suture. When the cerclage suture comes out of the body, two strands of suture that are the opposite ends of the suture come out of the body. In other words, as shown in FIG. 1, the cerclage suture is a suture forming a circle and being connected to be one. The cerclage suture may be made of a synthetic resin, such as nylon, or a metal wire (stainless steel, a metal coated with nylon, or the like). Further, the cerclage suture may be in the form of a wire that is made by twisting a plurality of fine wires. Assuming that the cerclage suture 10 is formed by twisting a plurality of wires, the cerclage suture is also called as "cerclage lope" or "cerclage wire", which is a kind of cerclage suture, thereby being within the spirit and scope of the invention.

The device for transcatheter treatment for tricuspid regurgitation of the present invention is configured such that a blocking part for blocking a space resulting from incomplete closure of the tricuspid valve. The device is added to a mitral valve cerclage tissue protection device for protecting cardiac tissues, such as the coronary sinus, the tricuspid valve, the interventricular septum, and the like, from the cerclage suture (cerclage lope) used in mitral valve cerclage coronary sinus annuloplasty.

The device of the present invention may be made of a synthetic resin, such as rubber or flexible plastic material, or a metal material, such as a coil spring.

The device of the present invention is made of a synthetic resin or a coil spring that is soft, flexible, and movable along with contractions of the heart, and has high flexibility, high stability, and high deliverability during cerclage coronary sinus annuloplasty. A coil spring device is coated with a biological adaptation material (ex. an ePTFE), thereby preventing the metal coil spring from coming into direct contact with a patient's body, reducing allergic reaction, and preventing hazards, such as thrombus caused when blood penetrates into between threads of the coil spring.

Hereinbelow, reference will be made to the coil spring device as an example of the device, with reference to FIGS. 1 and 2. However, the protective scope of the present invention should not be limited to the coil spring device.

A device 20 includes: a hollow coronary sinus tube 22 for engaging into coronary sinus tissue; a hollow tricuspid valve tube 24 for crossing over tricuspid valve tissue and anchoring at interventricular septum tissue; and a stem 26 where the coronary sinus tube and the tricuspid valve tube are laterally coupled with each other. In other words, the device includes: the hollow coronary sinus tube 22 for engaging into coronary sinus tissue; and the hollow tricuspid valve tube 24 for crossing over tricuspid valve tissue and anchoring at interventricular septum tissue, wherein the coronary sinus tube and the tricuspid valve tube are laterally coupled with each other from upper portions thereof by a predetermined length, and lower portions thereof are separated from each other. A wire of the tube has a thickness of about 0.5 mm, and the tube has an external diameter of about 2 mm.

The coronary sinus tube 22 serves to engage into the coronary sinus tissue from the cerclage suture by being inserted into the coronary sinus; and the tricuspid valve tube 24 serves to cross over the tricuspid valve tissue and to anchore at the interventricular septum tissue from the cerclage suture by being inserted into the tricuspid valve.

The manufacturing process of the device of the present invention using the coil spring is as follows. Firstly, after the coronary sinus tube 22 and the tricuspid valve tube 24 are separately made, lower portions of the coronary sinus tube 22 and the tricuspid valve tube 24 are bent to be curved. Next, upper portions of the coronary sinus tube 22 and the tricuspid valve tube 24 are laterally coupled with each other. The coronary sinus tube and the tricuspid valve tube are coupled by using the pressure of a press. More specifically, both the coronary sinus tube and the tricuspid valve tube are inserted into an additional rubber tube, and then the rubber tube is pressed by using the press.

In order for the device of the present invention to be used as a device for transcatheter treatment for tricuspid regurgitation, the lower portion of the tricuspid valve tube 24 is provided with a blocking part 30 for blocking a space resulting from incomplete closure of the tricuspid valve. In other words, the blocking part 30 is provided for blocking the tricuspid valve, namely, a reverse flow of blood from the right ventricle to the right atrium, and is disposed on a side of the tricuspid valve tube as shown in the drawings.

The blocking part may be in the form of a blocking membrane or a balloon. In the drawings, the blocking part is in the form of the blocking membrane, but not limited thereto.

The blocking membrane includes a support 34 and a body 32 having a membrane shape. In other words, the support 34 is provided for maintaining a shape of the blocking membrane by being connected to the tricuspid valve tube, and is in an annular shape or other shape. The body 32 is provided for blocking the blood flow by being connected to the support 34. The support 34 has a stronger structure than the body such that the shape of the blocking membrane is maintained.

Figure 3:
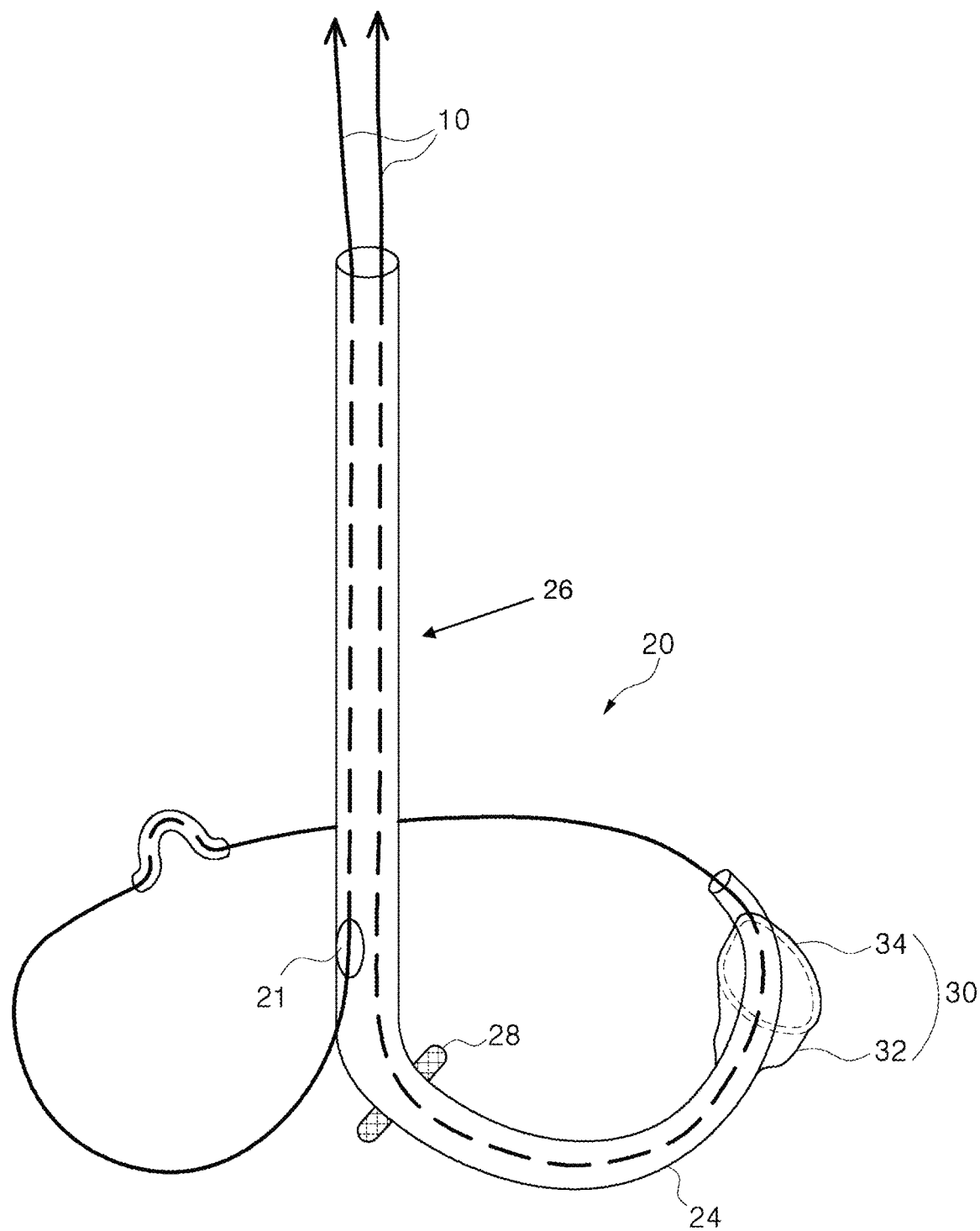
FIG. 3 is a perspective view showing a device for transcatheter treatment for tricuspid regurgitation according to another preferred embodiment of the present invention.

FIG. 3 is a perspective view showing a device for tricuspid regurgitation surgery according to another preferred embodiment of the present invention.

Referring to FIG. 3, the device for transcatheter treatment for tricuspid regurgitation shown in the drawing includes a hollow cylindrical tube for allowing a cerclage suture to be inserted thereinto, with a hole 21 being provided in a side of the cylindrical tube for allowing a cerclage suture inserted into a coronary sinus to come out from the cylindrical tube.

A lower portion of the hollow cylindrical tube below the hole is inserted into the tricuspid valve to cross over the tricuspid valve tissue and to anchore at the interventricular septum tissue; and the blocking part 30 is provided at an end portion of the cylindrical tube for blocking the tricuspid valve.

The hole 21 or a protrusion 28 may serve as a hinge portion in FIG. 1. In other words, when the cerclage suture having come out from the device 20 is inserted into the coronary sinus, a portion around the hole 21 or the protrusion 28 is hooked on an edge of a coronary sinus (CS) inlet. Thereby, the lower portion of the tricuspid valve tube, and the portion around the hole 21 or the protrusion 28 are locked, and a portion of the tricuspid valve tube therebetween is maintained in a reverse C shape, so the cylindrical tube is suspended around the tricuspid valve (TV), not coming into close contact therewith. This configuration provide a strong column that is obliquely crossing over coaptation zone of tricuspid valve leaflets in similar plane of tricuspid valve leaflet, and it also reduces the restriction of movement of leaflets. Herein, the blocking part 30 serves to block a space resulting from incomplete closure of the tricuspid valve, as in FIGS. 1 and 2.

Although preferred embodiments of the present invention have been described for illustrative purposes, those skilled in the art will appreciate that various modifications, additions and substitutions are possible, without departing from the scope and spirit of the invention as disclosed in the accompanying claims.

INDUSTRIAL APPLICABILITY

The present invention relates to a device for transcatheter treatment for tricuspid regurgitation, which may be applied to a device for patients suffering from tricuspid regurgitation, which is an abnormal reverse flow of blood from the right ventricle to the right atrium resulting from incomplete closure of the tricuspid valve between the right ventricle and the right atrium during contraction of the right ventricle of the heart.

The invention claimed is:

1. A device for transcatheter treatment for tricuspid regurgitation, the device comprising:
    a coronary tube having a first outer peripheral surface, the coronary tube configured for entering into a coronary sinus; and
    a tricuspid tube having a longitudinal axis, the tricuspid tube having a distal end and a second peripheral outer surface provided in contact with the first outer peripheral surface for a selected distance, and branching away from the first outer peripheral surface at a selected position spaced away from the distal end of the tricuspid tube, the tricuspid tube configured for extending through tricuspid valve tissue and anchoring at interventricular septum tissue, the tricuspid tube having a blocking part laterally attached on the tricuspid tube, the blocking part including an annular support and a membrane body, the annular support configured for maintaining a shape of the membrane body, the annular support extending crosswise to the longitudinal axis of the tricuspid tube such that the membrane body completely blocks a reverse flow of blood from the right ventricle to the right atrium resulting from incomplete closure of the tricuspid valve.

2. The device of claim 1, wherein the coronary tube and the tricuspid tube are made of either a metal coil spring or an elastic synthetic resin.

3. A device on a cerclage suture for transcatheter treatment for tricuspid regurgitation, the device comprising:
    a tricuspid tube having a longitudinal axis, the tricuspid tube having an outer peripheral surface, the tricuspid tube having a hole provided on the outer peripheral surface for allowing the cerclage suture inserted into a coronary sinus to come out from the tricuspid tube, the tricuspid tube having a blocking part provided laterally attached on the outer peripheral surface, the blocking part including an annular support and a membrane body, the annular support configured for maintaining a shape of the membrane body, the annular support extending crosswise to the longitudinal axis of the tricuspid tube such that the membrane body completely blocks a reverse flow of blood from the right ventricle to the right atrium resulting from incomplete closure of the tricuspid valve.

4. A device on a cerclage suture for transcatheter treatment for tricuspid regurgitation, the device comprising:
    a tricuspid tube having a longitudinal axis, the tricuspid tube having a a peripheral outer surface, the tricuspid tube configured for extending through tricuspid valve and anchoring at interventricular septum tissue, tricuspid tube having means laterally attached on the tricuspid tube for completely blocking a reverse flow of blood from the right ventricle to the right atrium resulting from incomplete closure of the tricuspid valve of a heart.

* * * * *